United States Patent
Nilsson et al.

(10) Patent No.: US 6,536,426 B1
(45) Date of Patent: Mar. 25, 2003

(54) ACTIVE WALLS

(75) Inventors: Thomas Nilsson, Mariefred (SE); Lars-Gunnar Nilsson, Koping (SE)

(73) Assignee: Microdrug AG, Hergiswil (CH)

( * ) Notice: Subject to any disclaimer, the term of this patent is extended or adjusted under 35 U.S.C. 154(b) by 143 days.

(21) Appl. No.: 09/665,064

(22) Filed: Sep. 19, 2000

(30) Foreign Application Priority Data

Dec. 8, 1999 (SE) .............................................. 9904484

(51) Int. Cl.$^7$ ............................................... B65D 83/06
(52) U.S. Cl. ..................... 128/203.15; 604/58; 128/898
(58) Field of Search ..................... 239/22, 650, 654, 239/104, 106; 604/57–64; 128/200.14, 200.24, 203.12, 203.15, 898

(56) References Cited

U.S. PATENT DOCUMENTS 4,852,561 A * 8/1989 Sperry .................... 128/200.23
4,889,114 A * 12/1989 Kladders ................ 128/203.15

* cited by examiner

*Primary Examiner*—Glenn K. Dawson
(74) *Attorney, Agent, or Firm*—Young & Thompson

(57) ABSTRACT

A powder distribution device for transporting and mixing a fine powder with a gas is disclosed. The device presents a distribution member forming a connection between a source of fine powder and a discharge opening. The distribution member has a first inlet portion (10) and an outlet portion (12) for a stream of a first gas (1) mixed with the fine powder. The main body of the distribution member constitutes a porous body portion (16) being surrounded by a second gas (2). If a pressure gradient is created between the second gas (2) and the first gas (1), i.e. the first gas (1) being at a slightly lower pressure, the second gas (2) will leak trough the porous body (16) and thereby preventing powder, in the mix of the first gas and fine powder, from sticking or clogging within the distribution member, which thereby forms an active non-sticking wall relative to of the fine powder.

6 Claims, 1 Drawing Sheet

ACTIVE WALLS

TECHNICAL FIELD

Figure 1:
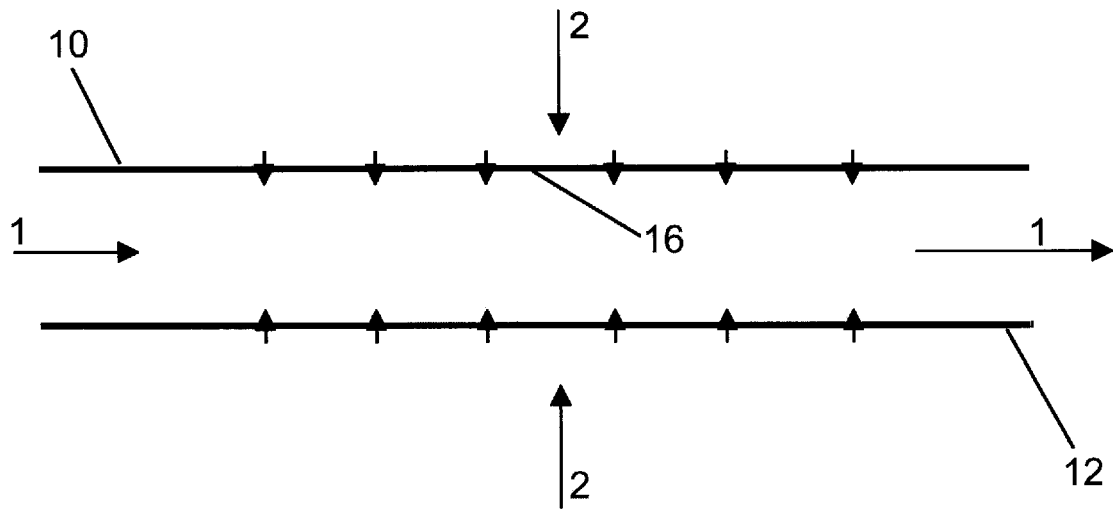
Figure 2:
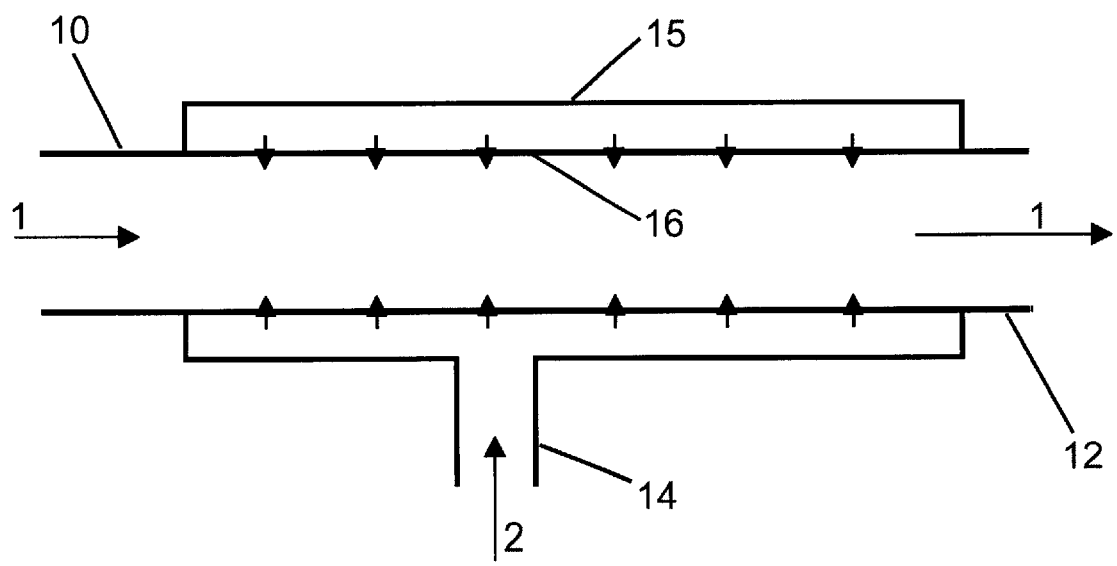

The present invention relates to a method and a device for minimizing the amount of a fine powder sticking to the walls of a distribution member carrying a mix of air and the powder.

BACKGROUND

Within some technical areas there is a problem in that some part of a fine powder mixed with a gas and subsequently transported by this gas, e.g. air, will stick to the walls of a distribution member when it passes through this distribution member. Instruments for measuring for instance the amount of powder mixed with a transporting gas as well as providing a measure of the grain size distribution often faces the problem that the different sizes powder grains to be measured will easily stick to the walls of a measurement channel. This implies that cleaning must be regularly performed when measuring, besides the accuracy of the measurement will be very dependent of how often measures for cleaning will be performed.

Another area facing a similar problem, for instance, is the administering of medical compositions by means of inhalers. Administering of medical powders today can be performed in numerous ways. Within health care more and more is focussed on the possibility of dosing medical drugs as a powder directly to the lungs of a patient by means of an inhaler to thereby obtain an effective, quick and patient-friendly administering of such substances.

For the medical powders, being administered by means of an inhaler, to land in the lungs, the powder should preferably have a grain size of 0.5 to 10 $\mu$m. A larger grain size will easily be sticking just in the mouth and throat, and a smaller grain size may accompany the expiration air out again.

Small grain size powder also has a strong tendency of agglomerating, i.e. to get conglomerated. In the inhalers, which are used today, a large extent of the active substance is in the form of agglomerates when it is dosed and much powder therefore will stick in the upper respiratory tract. Different ways to de-agglomerate the powder have been developed and in most cases the inhalation air is utilized for decomposing the agglomerates.

It is also common to use carriers having a larger grain size onto which the fine powder is distributed. Upon inspiration the large grains will then stick in the oral cavity while the small grains are set free and proceed to the lungs. Certain manufacturers also use electrically driven propellers, piezo-vibrators and/or mechanical vibration to decompose the agglomerates. Thus, achieving a very large portion of individual particles in the inspiratory air is a very important factor for obtaining a high degree of effectiveness upon inhalation. Yet another problem is that the medical composition powder also will stick to the walls of an inhaler distribution member normally connected to a suitable mouthpiece for the administration by means of an inspiration.

Therefore there is a demand of a solution which will to a large extent prevent particularly fine powder or its agglomerates from sticking to a distribution member, for instance, in a measuring instrument or an inhaler, which otherwise may be more or less clogged due to powder sticking to its walls.

SUMMARY

A powder distribution device for transporting and mixing of a fine powder with a gas is disclosed. The device presents a distribution member forming a connection between a source of fine powder and a discharge opening. The distribution member has a first inlet portion and an outlet portion for a stream of a first gas mixed with the fine powder. The main body of the distribution member constitutes a porous body portion being surrounded by a second gas. If a pressure gradient is created between the second gas and the first gas, i.e. the first gas being at a slightly lower pressure, the second gas will leak trough the porous body and thereby preventing powder, in the mix of the first gas and fine powder, from sticking or clogging within the distribution member, which thereby obtains an active non-sticking wall relative to of the fine powder.

A method according the present invention is set forth by the independent claim 1 and the dependent claim 2. A device according to the invention is set fort by the independent claim 3, and further embodiments of the device are set forth by the dependent claims 4 to 9.

BRIEF DESCRIPTION OF THE DRAWINGS

The invention, together with further objects and advantages thereof, may best be understood by making reference to the following description taken together with the accompanying drawings, in which:

FIG. 1 illustrates a distribution member according to the present invention for connection to a source of fine powder, and FIG. 2 illustrates a further embodiment of a distribution member according to the present invention to regulate the amount of the second gas to obtain a desired pressure gradient.

DETAILED DESCRIPTION

In FIG. 1 is presented an embodiment of a distribution member illustrating the present invention. Such a distribution member may be used, for instance, in a measuring instrument or may even be utilized in an inhaler device. In a measurement instrument the distribution member will be inserted between a source delivering a powder to be mixed with a gas transporting the powder for forming a measurement set-up. An instrument utilizing the distribution member could typically be a measurement set-up for measuring the size of the powder particles from the powder source as well as the distribution of particle sizes when transported by a gas flow. A typical such measurement for instance may utilize a laser beam, which will be scattered by the small grains of powder transported by the gas. In an inhaler the distribution member may be inserted between a source of powder and a mouthpiece used for the inspiration of powder.

An input side 10 of the distribution member is connected to a suitable powder source. Similarly an output side 12 of the distribution member is connected to an exhaust, which in the case of an inhaler would be a suitable mouthpiece for the inhalation. The main distribution member in an illustrative embodiment consists of, for instance, a tube having a porous body 16. A first gas 1 passing through the distribution member body contains a mixture of gas and powder, for instance a medical composition to be administered by means of an inhaler. The distribution member according to a first embodiment demonstrated in FIG. 1 is surrounded by a second gas 2. A pressure difference between the first gas 1 and the second gas 2 is normally obtained by creating an under-pressure in the first gas 1, for instance, by a suction of the first gas 1 from the outlet portion 12. When the second gas 2 is at a higher pressure compared to the first gas 1 the second gas 2 will leak trough the porous body portion 16 then preventing powder from sticking or clogging at the inner of the distribution member body.

In a second illustrative embodiment, for obtaining a desired pressure gradient, a second gas 2 is fed via a second inlet 14 in a second wall 15 into a space between the porous body 16 and the second wall 15. By regulating the amount of the second gas a desired pressure gradient will be obtained. The gas-flow passing through the distribution member will contain a mixture of the first gas 1 and a powder. This gas-flow then still presenting a lower pressure compared to the second gas 2 implies that the second gas 2 will leak through the porous body 16 and prevent powder from sticking to the inner wall of the porous body 16. A typical gas to be used in a measurement set-up will be air or in some set-ups dry air, but any other type of available gas may be used, for instance, even an inert gas may be used. A typical material for the distribution member body 16 is sintered porous plastic, but also porous sintered metal may be used. Preferably the material is conductive or electrostatic dissipative and connected to a device ground to prevent electrostatic charging. By balancing the pressure at the second gas inlet 14 against the pressure of the transportation gas 1, the second gas 2 when leaking through the porous body will also assist in further distributing the powder within the first gas 1. This is also valid in an inhaler device utilizing the present distribution member for improving the efficiency of the inhaler in which the pressure gradient is created by the suction of the first gas 1, in this case just ordinary air, when inhaling a medical composition powder mixed with air. In a further embodiment of an inhaler the entire portion of the inhaler case in contact with the powder to be administered may be formed of a porous material preferably enclosed in an outer shell. This outer shell then forming a space between an outer wall 15 and the inner porous body for obtaining a pressure gradient towards the interior of the device thereby, by means of the porous inner body 16, preventing powder grains from sticking to the inner body of the inhaler device.

It will be understood by those skilled in the art that various modifications and changes may be made to the present invention without departure from the scope thereof, which is defined by the appended claims.

What is claimed is:

1. A method for minimizing an amount of a powder sticking inside a body of a distribution member carrying a gas mixed with the powder, comprising the steps of:

providing the distribution member body comprising a material presenting a porous characteristic;

creating a pressure gradient such that a lower pressure is obtained in an inner portion of said distribution member body, whereby a surrounding gas leaks through the distribution member body thereby preventing particles of the powder from sticking to an inside of the distribution member body.

2. The method according to claim 1, comprising the further step of using for said distribution member body a sintered porous plastic or a porous sintered metallic material.

3. The method of claim 1, wherein the surrounding gas is air.

4. The method of claim 3, wherein the inner portion of the distribution member body contains air.

5. The method of claim 1, wherein the step of creating a pressure gradient comprises creating by suction an underpressure of the inner portion of the distribution member body with respect to the surrounding gas.

6. The method of claim 1, wherein the step of creating a pressure gradient comprises adjusting a pressure of the surrounding gas with respect to the inner portion of the distribution member body.

* * * * *